United States Patent [19]

Bates

[11] Patent Number: 4,826,683

[45] Date of Patent: May 2, 1989

[54] DECONGESTANT

[76] Inventor: Harry L. Bates, 311 W. Ave., Elmira, N.Y. 14904

[21] Appl. No.: 1,902

[22] Filed: Jan. 9, 1987

[51] Int. Cl.$^4$ .................. A61K 33/30; A61K 35/78
[52] U.S. Cl. ............................ 424/641; 424/195.1; 514/54; 514/458; 514/474; 514/725; 514/853
[58] Field of Search ............................ 424/195.1, 145; 514/458, 474, 725, 54, 853

[56] References Cited

U.S. PATENT DOCUMENTS 3,920,816  10/1975  Seegall et al. .................... 424/195.1

OTHER PUBLICATIONS

Hiday, Home Remedies, 1981, p. 5.
Lust, The Herb Book, pp. 476, 479, 1974.

*Primary Examiner*—John W. Rollins
*Attorney, Agent, or Firm*—L. Rita Quatrini

[57] ABSTRACT

A decongestant is disclosed consisting essentially of active components of from about 2 g to about 10 g of vegetable oil, from about 0.1 g to about 5 g of aloe vera, from about 3 mg to about 150 mg of zinc, from about 10 mg to about 1000 mg of vitamin C, from about 2,000 USP Units to about 70,000 USP Units of vitamin A, from about 20 IU to about 500 IU of vitamin E, from about 10 mg to about 300 mg of vitamin B-6, from about 50 mcg to about 2000 mcg of biotin, and from about 0.3 g to about 2 g of fruit pectin, per about 1 liter of the decongestant. The balance is carriers and solvents. The zinc is supplied as one or more therapeutic compounds of zinc.

7 Claims, No Drawings

DECONGESTANT

This invention relates to a decongestant. More particularly, it relates to a decongestant suitable for use as a nasal spray.

BACKGROUND OF THE INVENTION

There are a number of decongestant preparations on the market today. I have not found any that work effectively in relieving severe nasal and sinus congestion. I believe that this is so because most of them are not suitable by virtue of their specific components and compositions for direct application to the nasal passages without an inhaling device such as a plastic inhaler. Rather they are used in other ways, for example by inhaling steam or their vapors, etc. An example of this is a decongestant supplied by Richardson-Vicks Inc. under the trade name of Vicks VapoRub. According to the Physicians Desk Reference For Nonprescription Drugs First Edition, page 632, Vicks VapoRub is not to be placed in the nostrils. Decongestants that are designed to be applied to the nasal passages, for example, liquid spray preparations, I have found to be irritating.

SUMMARY OF THE INVENTION

In accordance with one aspect of this invention, there is provided a decongestant consisting essentially of active components of from about 2 g to about 10 g of vegetable oil, from about 0.1 g to about 5 g of aloe vera, from about 3 mg to about 150 mg of zinc, from about 10 mg to about 1000 mg of vitamin C, from about 2,000 USP Units to about 70,000 USP Units of vitamin A, from about 20 IU to about 500 IU of vitamin E, from about 10 mg to about 300 mg of vitamin B-6, from about 50 mcg to about 2000 mcg of biotin, and from about 0.3 g to about 2 g of fruit pectin, per about 1 liter of the decongestant. The balance is carriers and solvents. The zinc is supplied as one or more therapeutic compounds of zinc.

DETAILED DESCRIPTION OF THE INVENTION

For a better understanding of the present invention, together with other and further objects, advantages and capabilities thereof, reference is made to the following disclosure and appended claims in connection with the above description of some of the aspects of the invention.

This invention relates to a decongestant consisting essentially of active components in the following formulation per liter of decongestant:

| Component | Minimum Amount | Maximum Amount |
| --- | --- | --- |
| Vegetable oil | 2 g | 10 g |
| Aloe vera | 0.1 g | 5 g |
| Zinc | 3 mg | 150 mg |
| Vitamin C | 10 mg | 1000 mg |
| Vitamin A | 2,000 USP Units | 70,000 USP Units |
| Vitamin E | 20 IU | 500 IU |
| Vitamin B-6 | 10 mg | 300 mg |
| Biotin | 50 mcg | 2000 mcg |
| Fruit pectin (dry basis) | 0.3 g | 2 g | with the balance being carriers and solvents.

More preferably, the decongestant consists essentially of active components in the following formulation per liter of decongestant:

| Component | Minimum Amount | Maximum Amount |
| --- | --- | --- |
| Vegetable oil | 3 g | 8 g |
| Aloe vera | 0.6 g | 3 g |
| Zinc | 8 mg | 80 mg |
| Vitamin C | 60 mg | 600 mg |
| Vitamin A | 3500 USP Units | 25,000 USP Units |
| Vitamin E | 30 IU | 250 IU |
| Vitamin B-6 | 30 mg | 200 mg |
| Biotin | 100 mcg | 1200 mcg |
| Fruit pectin (dry basis) | 0.6 g | 1.5 g |

A still more preferred formulation of active components is as follows for 1 liter of decongestant:

| Component | Minimum Amount | Maximum Amount |
| --- | --- | --- |
| Vegetable oil | 4 g | 6 g |
| Aloe vera | 0.7 g | 2 g |
| Zinc | 10 mg | 40 mg |
| Vitamin C | 150 mg | 400 mg |
| Vitamin A | 5000 USP Units | 13,000 USP Units |
| Vitamin E | 40 IU | 200 IU |
| Vitamin B-6 | 40 mg | 150 mg |
| Biotin | 125 mcg | 800 mcg |
| Fruit pectin (dry basis) | 0.8 g | 1.3 g |

The most preferred formulation of active components is as follows for about 1 liter of decongestant:

| Component | Amount |
| --- | --- |
| Vegetable oil | 5 g |
| Aloe vera | .8 g |
| Zinc | 30 mg |
| Vitamin C | 300 mg |
| Vitamin A | 7000 USP Units |
| Vitamin E | 50 IU |
| Vitamin B-6 | 50 mg |
| Biotin | 400 mcg |
| Fruit pectin (dry basis) | 1 g |

Throughout this invention, the preferred solvent and carrier is water. Most preferred is distilled water because of its purity.

In actuality, any source of aloe vera can be used as there are a number of preparations available today. Also the juice and/or gel from the aloe vera plant can be used. I prefer to use a preparation of aloe vera gel which is about 99.6% by weight aloe vera as the source of aloe vera.

Vitamin C can be used in the form of ascorbic acid or an ascorbate such as sodium ascorbate which is available commercially as a powder or in tablets.

The zinc is supplied in the form of one or more therapeutic zinc compounds. The term "therapeutic" as used in this invention in reference to zinc compounds means zinc compounds which can be used without harmful effects or which are considered to be non-toxic. These compounds can be any such preparation available such as zinc oxide, zinc salts, and preferably organic compounds of zinc such as zinc gluconate.

The source of biotin based compounds can be biotin itself or biotin in a chemically bound form.

The source of vitamin B-6, can be pyridoxine, pyridoxol, pyridoxamine, or any source.

The source of fruit pectin can be any source available. However, for ease of handling I prefer to use a commercial preparation of solubilized fruit pectin supplied by General Foods under the trade name of "Certo". Generally I use about 3 ounces of Certo to supply approximately 7 g of fruit pectin on a dry basis. In such cases, the liquid portion of the solubilized fruit pectin becomes part of the carriers and solvents portion of the decongestant.

The source of vitamin A can be any source available and this can be the water soluble form or in the form of an oil.

The source of vitamin E, tocopherol, is preferably predominately alpha tocopherol.

The vegetable oils are present to aid in expelling mucous. Vegetable oils are obtained from plants. Some vegetable oils that can be used in the decongestant are soybean oil, wheat germ oil, corn oil, olive oil, linseed oil, peanut oil, almond oil, sesame oil, sunflower oil, etc. and combinations of these. Soybean oil is preferred because of its light color.

It is to be understood that in addition to the above named components, the preparation can contain other ingredients such as aromatic oils, preservatives, emulsifiers, colorants, fragrances etc., if deemed appropriate, without departing from the scope of the invention. The addition of these additional components does not detract from the benefits of the present invention and they can be present in minor amounts. The total amount of these additional components is preferably no greater than about 5% by weight of the total decongestant preparation.

The decongestant can be prepared by any method which results in the components being uniformly blended without departing from the scope of the invention. The amounts of the active components have been given for a total of about 1 liter of decongestant. However, it is to be understood that the amounts can be adjusted proportionately depending on the total amount of decongestant which is to be prepared. For example, for a total of about 2 liters of decongestant, the amounts of the active components would be double the amounts given, and the solvents and carriers would be added to give a total of about 2 liters of the decongestant. Or, for about ½ liter of the decongestant, the amounts of active components would be about one-half the amounts given for the 1 liter, and the solvents and carriers would be added to give a total of about ½ liter of the decongestant. Since the relative amounts of components vary from the microgram range to the gram range, it is desirable in some cases to make up pre-mixes of individual components and then take aliquots of the pre-mixes in making up the decongestant. This insures that the correct amounts of components are measured and that the components are more uniformly dispersed in the decongestant.

Since the decongestant contains both organic and aqueous phases, it is desirable to shake the preparation just prior to use to insure that the preparation is homogeneous.

The decongestant preparations of this invention are particularly suitable for use as nasal sprays. I have found that they are not irritating to the nasal passages. The decongestant formulation of this invention results in clearing up of the nasal passages.

While there has been shown and described what are at present considered the preferred embodiments of the invention, it will be obvious to those skilled in the art that various changes and modifications may be made therein without departing from the scope of the invention as defined by the appended claims.

What is claimed is:

1. A decongestant consisting essentially of active components in the following formulation per liter of decongestant:

| Component | Minimum Amount | Maximum Amount |
|---|---|---|
| Vegetable oil | 2 g | 10 g |
| Aloe vera | 0.1 g | 5 g |
| Zinc | 3 mg | 150 mg |
| Vitamin C | 10 mg | 1000 mg |
| Vitamin A | 2,000 USP Units | 70,000 USP Units |
| Vitamin E | 20 IU | 500 IU |
| Vitamin B-6 | 10 mg | 300 mg |
| Biotin | 50 mcg | 2000 mcg |
| Fruit pectin (dry basis) | 0.3 g | 2 g | with the balance being water, and with said zinc being supplied as one or more therapeutic compounds of zinc.

2. A decongestant of claim 1 having additional components selected from the group consisting of a preservative, an emulsifier, and one or more aromatic oil said additional components being present in a concentration of no greater than about 5% by weight of said decongestant.

3. A decongestant of claim 1 wherein said active components are in the following formulation:

| Component | Minimum Amount | Maximum Amount |
|---|---|---|
| Vegetable oil | 3 g | 8 g |
| Aloe vera | 0.6 g | 3 g |
| Zinc | 8 mg | 80 mg |
| Vitamin C | 60 mg | 600 mg |
| Vitamin A | 3500 USP Units | 25,000 USP Units |
| Vitamin E | 30 IU | 250 IU |
| Vitamin B-6 | 30 mg | 200 mg |
| Biotin | 100 mcg | 1200 mcg |
| Fruit pectin (dry basis) | 0.6 g | 1.5 g |

4. A decongestant of claim 3 having additional components selected from the group consisting of a preservative, an emulsifier, and one or more aromatic oil said additional components being present in a concentration of no greater than about 5% by weight of said decongestant.

5. A decongestant of claim 3 wherein said active components are in the following formulation:

| Component | Minimum Amount | Maximum Amount |
|---|---|---|
| Vegetable oil | 4 g | 6 g |
| Aloe vera | 0.7 g | 2 g |
| Zinc | 10 mg | 40 mg |
| Vitamin C | 150 mg | 400 mg |
| Vitamin A | 5000 USP Units | 13,000 USP Units |
| Vitamin E | 40 IU | 200 IU |
| Vitamin B-6 | 40 mg | 150 mg |
| Biotin | 125 mcg | 800 mcg |
| Fruit pectin (dry basis) | 0.8 g | 1.3 g |

6. A decongestant of claim 5 having additional components selected from the group consisting of a preservative, an emulsifier, and one or more aromatic oil said additional components being present in a concentration of no greater than about 5% by weight of said decongestant.

7. A decongestant of claim 1 wherein said vegetable oil is selected from the group consisting of soybean oil, wheat germ oil, corn oil, olive oil, linseed oil, peanut oil, almond oil, sesame oil, sunflower oil, and combinations thereof.

* * * * *